United States Patent
Copelan

(10) Patent No.: US 6,620,384 B2
(45) Date of Patent: Sep. 16, 2003

(54) DOUBLE HANDHOLD TO PREVENT URINE-TEST CHEATING

(76) Inventor: Herbert W. Copelan, 875 E. Camino Real 14-E, Boca Raton, FL (US) 33432-6378

( * ) Notice: Subject to any disclaimer, the term of this patent is extended or adjusted under 35 U.S.C. 154(b) by 0 days.

(21) Appl. No.: 10/042,471

(22) Filed: Jan. 10, 2002

(65) Prior Publication Data

US 2003/0129096 A1 Jul. 10, 2003

(51) Int. Cl.[7] ................................................. B01L 3/00
(52) U.S. Cl. ........................ 422/102; 422/61; 422/939; 600/573; 206/807
(58) Field of Search ............................ 422/61, 99, 102, 422/939; 436/174, 180, 901; 600/573, 574; 206/807

(56) References Cited

U.S. PATENT DOCUMENTS

| | | | | |
|---|---|---|---|---|
| 4,769,215 A | * | 9/1988 | Ehrenkranz | 422/58 |
| 5,039,616 A | * | 8/1991 | Copelan | 436/56 |
| 5,069,878 A | * | 12/1991 | Ehrenkranz | 422/61 |
| 5,133,935 A | * | 7/1992 | Copelan | 422/61 |
| 5,179,027 A | * | 1/1993 | Fisher | 436/56 |
| 5,223,221 A | * | 6/1993 | Copelan | 422/61 |
| 5,352,410 A | * | 10/1994 | Hansen et al. | 422/58 |
| 5,603,903 A | * | 2/1997 | Copelan | 422/104 |
| 6,331,278 B1 | * | 12/2001 | Copelan | 422/102 |
| 6,409,971 B1 | * | 6/2002 | Wilkinson et al. | 422/103 |

* cited by examiner

Primary Examiner—Maureen M. Wallenhorst

(57) ABSTRACT

An improved double handhold to prevent urine-test cheating. The device restrictively engages each of a subject's hands so that neither is free to insert a false specimen into a container. The container is housed in one of the two hollow, single-handhold units that assemble end-to-end to form the double handhold and enclose the container. Before separating the two units for access to the container, the subject grasps each handhold and does not let go until after voiding and reassembling the device. Each handhold unit has contact sensors to detect one hand's engagement. An assembly sensor on each unit detects its separation from the other unit. A signal on each unit indicates any breach of hand restriction that occurs while the units are separate. The subject, therefore, can not secretly use a hand to insert a false specimen. Previous handhold apparatus used a latch system to require hand engagement to separate and reassemble the units. Latch systems indicate a breach of hand engagement by mechanically blocking the reassembly. Latch-system handholds are costly, less convenient for voiding, risk injury to the subject, less reliable in operation, more difficult to keep clean, more subject to cross-contamination, not instantaneous in action, and easier to circumvent. The improved device solves these problems and makes the double handhold practical and affordable.

5 Claims, 5 Drawing Sheets

US 6,620,384 B2

DOUBLE HANDHOLD TO PREVENT URINE-TEST CHEATING

FIELD OF INVENTION

This invention relates to collecting urine specimens for drug-abuse testing, specifically to double-handhold apparatus that restricts a subject's hands to prevent cheating.

DESCRIPTION OF PRIOR ART

The double handhold, as taught in U.S. Pat. No. 6,331,278 (2001) to Copelan, uses the operation of a latch system to indicate whether a subject keeps both hands restrictively engaged while a specimen container is exposed. The container is housed in one of the device's two single-handhold units. Grasping both units unlatches the assembly, allowing the units to separate for access to the container. If a hand disengages while the units are still separate, the latch system locks, the units do not fit back together, and the breach is evident.

Latch-systems are not ideal for a small device or one that places the container within the hand: They are costly to make and install, too large, easily soiled, and not always reliable mechanically. They require strong structure to resist forcing, are not instantaneous, and can be circumvented by blocking a latch element.

ADVANTAGES OF PRESENT INVENTION

Instead of a latch system, the improved double handhold uses a direct signal to indicate a breach of hand engagement. Modern sensors and signals and the necessary switches and circuitry are inexpensive to make and install. All components may be sealed and protected from urine spillage. The elements are small, do not require strong structure, and are reliable in operation. Without the space or strength requirements of a latch system, the new handhold's units are thin-walled so that the container is as convenient to void into as a container by itself. Not having a latch system's projections, apertures, and moving parts, the device is easier to position, poses no risk of discomfort or injury, is easier to clean and maintain, looks to be and is more hygienic, is less susceptible to cross contamination, reacts instantaneously, and is more difficult to circumvent.

DRAWING FIGURES

Closely related figures have the same number but different alphabetical suffixes.

Figure 1A:
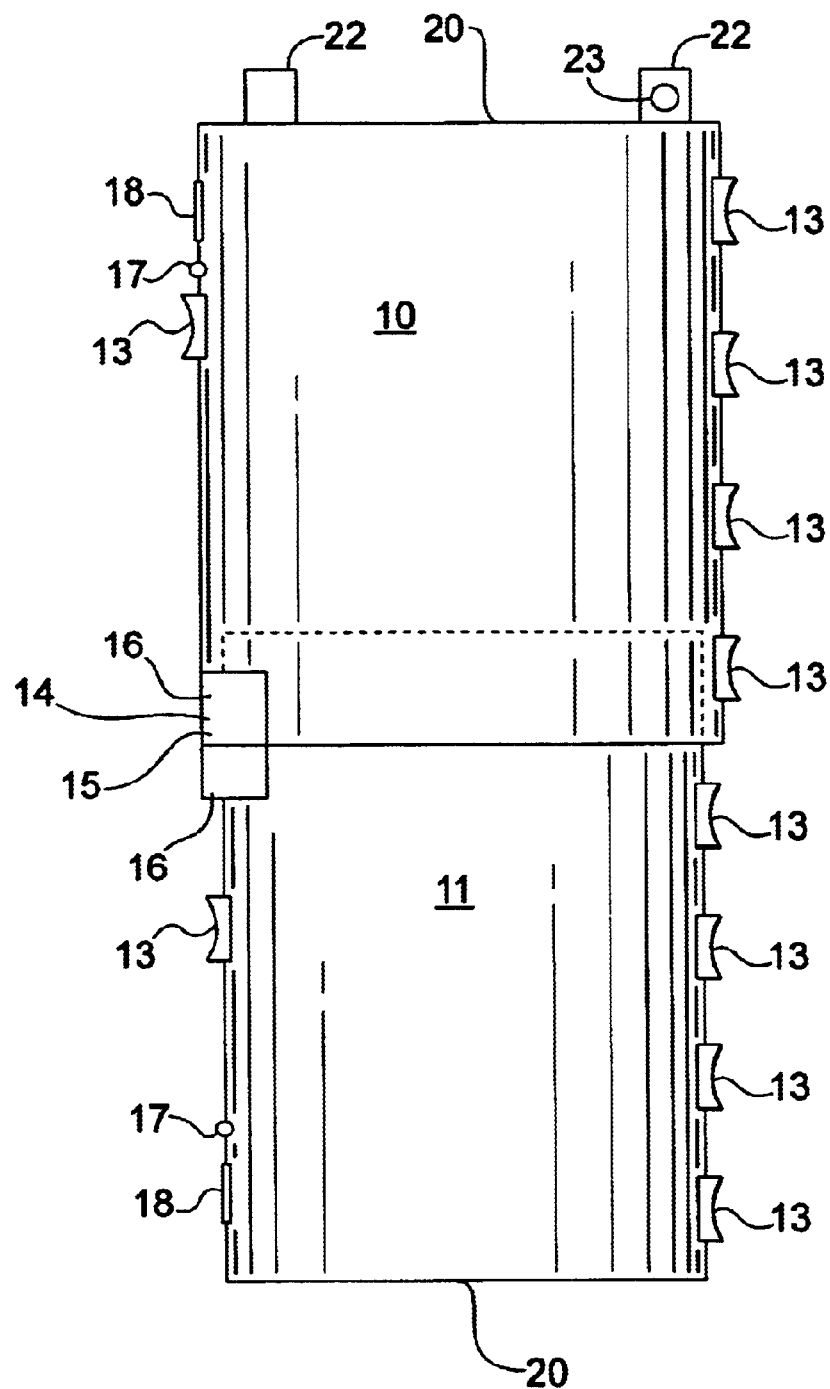
FIGS. 1A and 1B are side and back views of the assembled double handhold showing its two units.

REFERENCE NUMERALS IN DRAWINGS 10 upper unit
11 lower unit
12 container
13 digit sensor
14 assembly sensor
15 assembly terminal
16 guide
17 breach signal
18 keyhole
19 compartment
20 access door
21 shield
22 lug
23 lug hole
24 switch
25 transmitter

DESCRIPTION—FIGS. 1 TO 4

The preferred embodiment of the improved double handhold consists of two single handhold units reversibly assembled end-to-end, forming a cylinder about 25 cm. (10 inches) long. Each of the two units is closed at its free end and open at its assembling end. One unit holds a specimen container with its open end toward the open end of the unit. The other unit blocks access to the container when the units are assembled together. Separating the units allows access to the container. Each unit has digit sensors to detect engagement of one hand and an assembly sensor to detect the unit's engagement with an assembly terminal on the other unit. A signal on each unit indicates any breach of hand engagement that occurs at any time that the units are not assembled together.

FIG. 1A is a side view of the assembled units. Upper unit 10 telescopes part way over lower unit 11 for stability. Dashed lines indicate the telescoped, projecting portion of lower unit 11. Upper unit 10 encloses the open end of lower unit 11 and blocks access to specimen container 12 (seen in FIG. 2). Digit sensors 13 detect contact with each thumb and finger. Digit-sensor surfaces are concave for easy engagement by the digits. A two-part guide 16 facilitates apposition and rotational alignment of the units. Breach signal 17 indicates a lapse of proper hand restriction. Keyhole 18 admits a key (not shown) to reset breach signal 17.

Figure 1B:
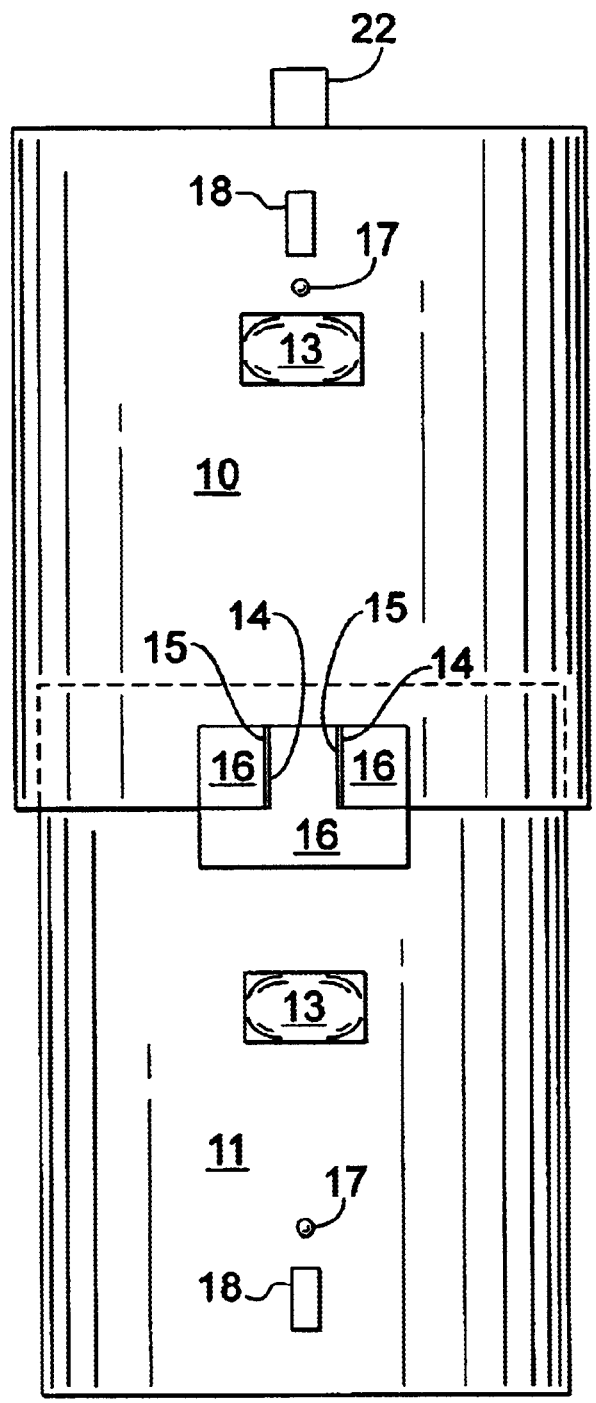

FIG. 1B is a back view of the device showing a digit sensor 13 on each unit and guide 16 as seen by a subject grasping or assembling the units. Each one of the two parts of guide 16 has one assembly sensor 14 to detect contact with assembly terminal 15 on the part of guide 16 on the other unit.

Figure 2:
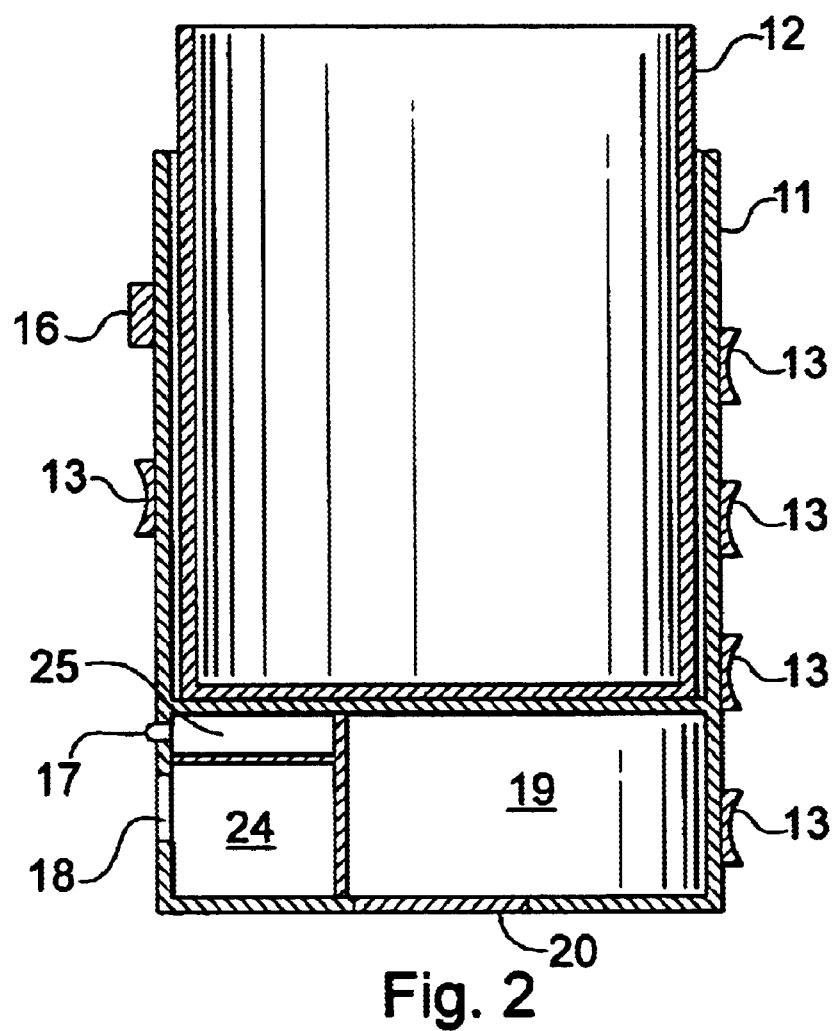
FIG. 2 is a cross-sectional side view of the lower unit.

FIG. 2 is a cross section of lower unit 11 with specimen container 12 in place. The base of lower unit 11 has a compartment 19 and access door 20, preferably operable by the reset key. Compartment 19 accommodates a switch 24 for breach signal 17, an optional transmitter 25, and a battery, preferably rechargeable (not shown). Upper unit 10 has a similar compartment in its base.

Figure 3A:
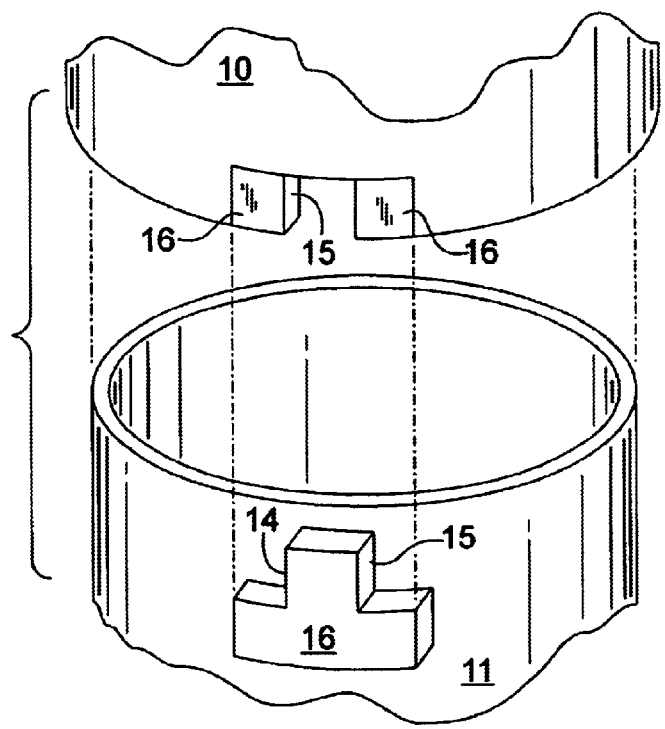
FIGS. 3A and 3B are frontal and side views of the two-part guide.
Figure 3B:
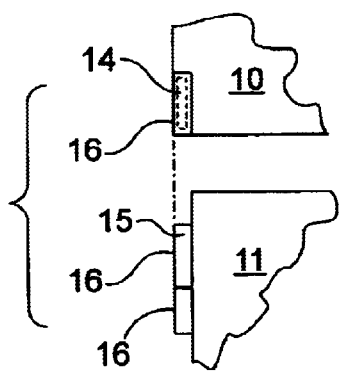

FIGS. 3A and 3B show guide 16, assembly sensor 14, and assembly terminal 15 frontally and in profile. The guide's bottom element on lower unit 11 fits the recess of its top element in the overlapping section of upper unit 10.

Figure 4A:
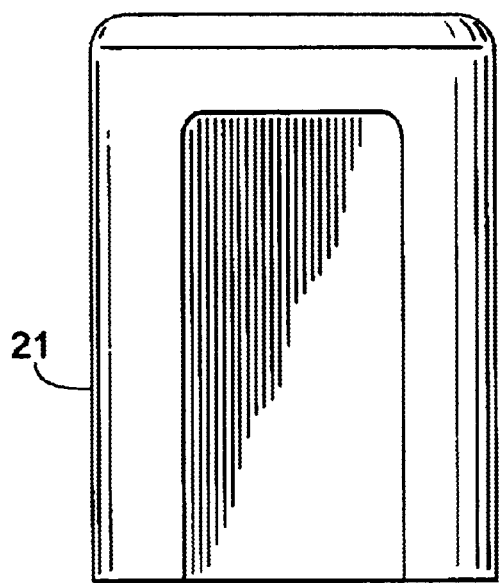
FIGS. 4A and 4B show an optional shield for protecting sensors from tampering.
Figure 4B:
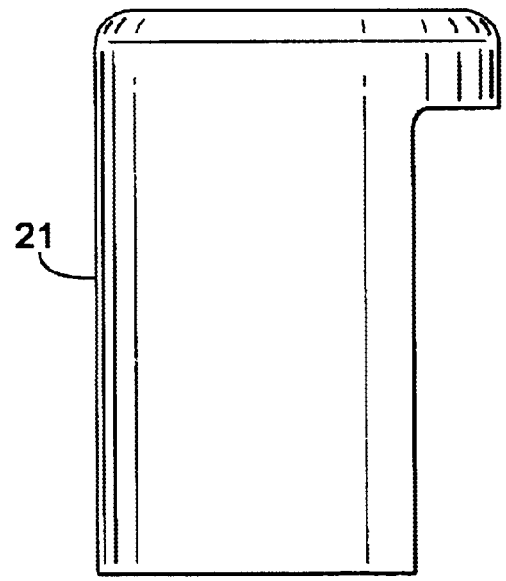

FIGS. 4A and 4B show cylindrical shield 21 from the back and side. Openings in the shield's top admit lugs 22 (on upper unit 10 in FIGS. 1A and 1B) to position and secure shield 21 with a padlock through lug hole 23. Shield 21 extends down over lower unit 11, but its open bottom allows lower unit 11 to be withdrawn. Its vertical gap allows the subject to grasp the handholds.

Operation—FIGS. 1 to 3

In each of the two units, the sensors are connected by conventional printed circuitry (not shown) to switch 24, which controls breach signal 17. An assembly circuit requires contact of assembly sensor 14 with its assembly terminal 15 on the other unit. A hand-contact circuit, in parallel with the assembly circuit, requires hand contact with all of the unit's digit sensors 13, which are connected in series. If any one of a unit's digit sensors is not contacted at any time while the units are separate, switch 24 sets breach signal 17 to indicate the breach. Switch 24 can then reset signal 17 only with the reset key. Therefore, the subject must engage one hand on each single-handhold unit before separating the two units and must maintain each engagement until the units are again assembled together and the container is no longer exposed.

Procedure for Use

An attendant prepares the device by separating the two units, removing any used specimen container 12, flushing the device if necessary, and inserting a fresh container.

The attendant demonstrates the device to the subject, explaining hand engagement, separation and assembly of the units, location and use of the container, preventing spillage by keeping the handhold upright after use, and the necessity for continuous hand engagement throughout the entire period of separation.

The attendant reassembles the units and resets breach signal 17. For any hygienic concerns, the attendant may cover each unit with a thin, transparent, disposable wrap. Next, the attendant hands the device to the subject, who is then allowed complete privacy.

When alone, usually in a lavatory, the subject puts the device down and adjusts clothing in preparation to void. When ready, the subject picks up the device, engages both hands on digit sensors 13, separates the units, voids a specimen, and reassembles the units. The subject places the device in an upright position, readjusts clothing, and returns the device to the attendant.

The attendant checks each unit's breach signal 17. It will be on if any of the unit's digit sensors 13 was not engaged at any time that the units were separate. This would indicate that a hand might have been free to insert a false specimen.

Options

Shield 21 is not required ordinarily because tampering with a sensor is unlikely if its contact area is small, concave, or protected by ridging. As seen from FIG. 4, shield 21 attaches to upper unit 10 but also protects lower unit 11 because both hands are engaged before unit 11 is withdrawn through the shield's open bottom and exposed. (Not engaging both hands beforehand would activate breach signal 17.) Shield 21 is transparent to facilitate hand placement. The thickness of the wall around container 12 is unchanged and voiding remains convenient. Shield 21 must be removed to service the device for each test.

Besides shielding, other options are available to protect against tampering: Temperature- or fingerprint-sensitive digit sensors are possible. A timer connected to breach signal 17 could limit the time for engaging both hands.

To circumvent any hand-restricting device, a subject may attempt to introduce a false specimen from a small flask secretly placed in the mouth. A surgical type mask secured with non-reusable ties blocks such attempts.

Guide 16, inverted from the original device, allows snug telescoping with little chance of faulty assembly or accidental separation. An external latch, freely accessible before hand engagement, would encumber the handholds. If desired, breach signal 17, or additional signals, can be connected to flash or otherwise alert the subject to improper hand engagement before separating the units or to indicate improper assembly before removing the hands after using the device. If innocent activation of breach signal 17 does occur, the attendant simply resets it.

Other options and variations from the preferred embodiment are feasible: For example, the reset key for breach signal 17 is not necessary if a reset code is programmed for digit sensors 13. Transmitter 25 can be added to the circuitry to allow remote monitoring. Circuitry may be wired rather than printed. The entire system could be mechanical, using hand motion to detect contact, unit displacement for assembly, and hand power instead of an electrical system.

For fabricating the double handhold, impervious materials are preferred. Plastics, composites, metals, and alloys are practical.

The description above is meant to explain the invention and illustrate its embodiment, not to limit its scope. For example, the units, assembly joint, sensors, signals, switches, guides, compartments, and access doors may have various configurations, dispositions, and mechanisms. The scope of this invention, therefore, should be determined by the claims and their equivalents.

I claim:

1. A double handhold comprising two single handhold units reversibly assembled together, wherein a first single handhold unit accommodates a specimen container for a subject's urine and a second single handhold unit prevents access to said specimen container when said two single handhold units are assembled together, and wherein each one of said two single handhold units comprises:

a) sensing means for detecting its assembly to the other one of said two single handhold units, b) sensing means for detecting its engagement by one of said subject's two hands, c) signaling means for indicating a breach of said engagement by one of said subject's two hands when the unit is not assembled to the other one of said two single handhold units, said signaling means connected to both said sensing means, and d) switching means connected to both said sensing means, said switching means operable to set said signaling means to indicate said breach of said engagement by one of said subject's two hands, but not operable by reengagement of said subject's hand to one or both of the single handhold units to reset said signaling means so that said subject cannot manipulate said double handhold so that it would not indicate that any said breach had occurred; whereby said double handhold signals if one of said subject's two hands may have had access to said specimen container during collection of a sample of the subject's urine therein.

2. The double handhold of claim 1 and further including shielding means for preventing tampering with said sensing means for detecting the engagement of each of said two single handhold units by one of said subject's two hands.

3. The double handhold of claim 1 and further including shielding means for preventing tampering with said sensing means for detecting the assembly of one of said single handhold units to the other one of said two single handhold units.

4. The double handhold of claim 1 and further including for each one of said two single handhold units a timing means for detecting a delay between activation of said sensing means for detecting the assembly of one of said single handhold units to the other of said two single handhold units and activation of said sensing means for detecting the engagement of each of said two single handhold units by one of said subject's two hands; whereby opportunity for tampering is limited in time.

5. A double handhold comprising two single handhold units reversibly assembled together, wherein a first single handhold unit accommodates a specimen container for a subject's urine and a second single handhold unit prevents access to said specimen container when said two single handhold units are assembled together, and wherein each one of said two single handhold units comprises:

a) sensing means for detecting its assembly to the other one of said two single handhold units, b) sensing means for detecting its engagement by one of said subject's two hands, and c) signaling means for indicating a breach of said engagement by one of said subject's two hands when the unit is not assembled to the other one of said two single handhold units, said signaling means connected to both said sensing means, wherein said double handhold does not contain any latch means for locking the two single handhold units together when assembled to one another.

* * * * *